US011426505B2

(12) United States Patent
Sjöholm

(10) Patent No.: US 11,426,505 B2
(45) Date of Patent: Aug. 30, 2022

(54) APPARATUS AND METHOD FOR CONTACTING BLOOD WITH OZONE

(71) Applicant: Sangair AB, Lund (SE)

(72) Inventor: Johan Sjöholm, Lund (SE)

(73) Assignee: Sangair AB, Lund (SE)

( * ) Notice: Subject to any disclaimer, the term of this patent is extended or adjusted under 35 U.S.C. 154(b) by 11 days.

(21) Appl. No.: 16/815,997

(22) Filed: Mar. 11, 2020

(65) Prior Publication Data
US 2020/0276382 A1    Sep. 3, 2020

Related U.S. Application Data

(63) Continuation of application No. 15/511,194, filed as application No. PCT/SE2015/050964 on Sep. 15, 2015, now abandoned.

(30) Foreign Application Priority Data

Sep. 15, 2014  (SE) .................. 1451072-1

(51) Int. Cl.
A61M 1/36    (2006.01)
A61L 2/02    (2006.01)
A61L 2/00    (2006.01)

(52) U.S. Cl.
CPC ......... A61M 1/3687 (2013.01); A61L 2/0094 (2013.01); A61L 2/022 (2013.01); A61M 1/36 (2013.01); A61L 2202/22 (2013.01); A61M 2202/0216 (2013.01); A61M 2205/36 (2013.01); A61M 2205/3606 (2013.01); B01F 2215/0431 (2013.01)

(58) Field of Classification Search
None
See application file for complete search history.

(56) References Cited

U.S. PATENT DOCUMENTS

| 6,027,688 | A | 2/2000 | Wainwright |
| 6,096,219 | A | 8/2000 | Green et al. |
| 2003/0118473 | A1 | 6/2003 | Sunnen et al. |
| 2005/0051497 | A1 | 3/2005 | Latino et al. |
| 2005/0189302 | A1 | 9/2005 | Latino et al. |

(Continued)

FOREIGN PATENT DOCUMENTS

| CA | 2481144 A1 | 10/2003 |
| CN | 1660452 A | 8/2005 |

(Continued)

OTHER PUBLICATIONS

WIPO, Swedish International Search Authority, International Search Report and Written Opinion dated Dec. 15, 2015 in International Patent Application No. PCT/SE2015/050964, 18 pages.

(Continued)

Primary Examiner — David C Mellon
(74) Attorney, Agent, or Firm — Inskeep IP Group, Inc.

(57) ABSTRACT

An apparatus, system, and method for contacting blood with ozone to kill microorganisms in the blood are described. The method involves injecting microbubbles of ozone containing gas into a flow of blood, preferably at a temperature of less than 12° C. The apparatus includes a blood flow conduit including a blood ozone contacting portion including a porous ozone injector.

13 Claims, 3 Drawing Sheets

(56) References Cited

U.S. PATENT DOCUMENTS

| | | |
|---|---|---|
| 2010/0145248 A1 | 6/2010 | Myrick et al. |
| 2010/0192807 A1 | 8/2010 | Mathur et al. |
| 2011/0192807 A1* | 8/2011 | Conger ............... B01J 8/0457 |
| | | 210/150 |
| 2012/0228396 A1 | 9/2012 | Osborn et al. |
| 2016/0008525 A1 | 1/2016 | Elliot |

FOREIGN PATENT DOCUMENTS

| | | |
|---|---|---|
| EP | 0385320 A2 | 9/1990 |
| EP | 1386625 A1 | 2/2004 |
| JP | H08225094 A | 9/1996 |
| JP | H08225095 A | 9/1996 |
| JP | 2007278003 A | 10/2007 |
| WO | WO 1993/15779 A1 | 8/1993 |
| WO | WO 1996/17635 A1 | 6/1996 |
| WO | WO 1996/24386 A1 | 8/1996 |
| WO | WO 2000/38758 A1 | 7/2000 |
| WO | WO 2000/75083 A1 | 12/2000 |
| WO | WO 2004/041314 A1 | 5/2004 |
| WO | WO 2007/115412 A1 | 10/2007 |
| WO | WO 2008/066470 A1 | 6/2008 |
| WO | WO 2011/162805 A2 | 12/2011 |
| WO | WO 2013/082717 A1 | 6/2013 |
| WO | WO 2014/083284 A1 | 6/2014 |

OTHER PUBLICATIONS

Canadian Patent Office, Office Action dated Oct. 19, 2021 in Canadian Patent Application No. 2,967,307, 6 pages.

* cited by examiner

APPARATUS AND METHOD FOR CONTACTING BLOOD WITH OZONE

RELATED APPLICATIONS

This application is a continuation of and claims priority to U.S. patent application Ser. No. 15/511,194 filed Mar. 14, 2017 entitled Apparatus And Method For Contacting Blood With Ozone, which is the U.S. National Phase of and claims priority to International Patent Application No. PCT/SE2015/050964, International Filing Date Sep. 15, 2015, entitled Apparatus And Method For Contacting Blood With Ozone; which claims benefit of the Swedish Patent Application Serial No. 1451072-1, filed Sep. 15, 2014 entitled Apparatus And Method For Contacting Blood With Ozone, all of which are hereby incorporated by reference in their entireties.

FIELD OF THE INVENTION

The present invention relates to methods and apparatus for treating biological fluids with ozone. More particularly, the invention pertains to methods and apparatus for treating blood with ozone.

BACKGROUND OF THE INVENTION

Ozone is a strong oxidizing agent that has been used as a disinfectant. Despite the corrosive and highly reactive nature of ozone, the use of ozone to kill or inactivate certain infectious agents in blood has been explored. For example, US 2005/0189302 A1 discloses a method of inactivating viruses in blood by exposing the blood to ozone in a gas-fluid contacting device that maximizes gas-fluid mass transfer. The contacting device contains spheres or rods to form a thin film of blood and treatment is preferably performed at ambient temperature. WO 2011/162805 A2 discloses methods for inactivating infectious prion proteins in blood by subjecting blood to an ozone/oxygen admixture using a gas-fluid contacting device similar to that disclosed in US 2005/0189302 A1.

WO 93/15779 A1 discloses a method of increasing the nitric oxide concentration in the blood by contacting a sample of blood with ozone gas and ultraviolet radiation. The treated sample of blood is administered to a patient to treat a variety of conditions including bacterial, fungal, viral, and protozoal infection. The blood sample is most preferably a volume of 1 to 50 mL and is most preferably treated at a temperature of 42.5° C. for approximately 3 minutes.

U.S. Pat. No. 6,027,688 discloses a method for inactivating viruses, bacteria, fungi and protozoa in blood by contacting a flow of blood with counter-flow of an ozone-oxygen mixture for about 16 seconds using a gas-liquid contact apparatus.

Treating milk and other liquid foodstuffs with ozone to kill bacteria is known. WO 2008/066470 discloses a method for inhibiting bacterial growth in milk by exposing the milk to a finely divided gas stream containing ozone at ambient temperature. The method of ozonation disclosed in WO2008/066470 can be improved regarding efficiency. Also, the temperature of the liquid ozonized is ambient temperature. The ambient temperature may be an ambient storage and transport temperature, but the temperature at the ozonation location is not disclosed as needing temperature control in the method disclosed in WO2008/066470.

Although ozone has been used for killing microbes in large volumes of dairy products, such methods would destroy blood cells and inactivate enzymes and other proteins in the blood.

There is a need for methods and apparatus to treat and prevent serious bacterial, fungal, and viral infections that are not susceptible to treatment by conventional means such as antibiotic, antifungal, and antiviral drugs. Although ozone is known to kill microbes in blood, previously described methods do not provide adequate microbe killing without damaging the blood. Thus, there is a need for apparatus and methods for ozonating blood in a way that kills microbes in the blood of a patient without damaging blood cells or interfering with the normal function of blood in the patient. Related apparatus and method may also be used to ozonate blood before and/or after storage to kill microbes in the blood before storage and/or administration to a patient. Human and nonhuman animal patients suffering, for example, from microbial infection in the blood would benefit from such apparatus and methods, particularly in cases where convention drug therapy is not effective. Hence, an improved system, apparatus, and method for contacting blood with ozone would be advantageous.

SUMMARY OF THE INVENTION

Embodiments of the present invention preferably seek to mitigate, alleviate or eliminate one or more deficiencies, disadvantages or issues in the art, such as the above-identified, singly or in any combination by providing an apparatus for contacting blood with ozone, an ozonation system comprising the apparatus, and a method for contacting blood with ozone, according to the appended patent claims. While the invention is described with respect to the ozonation of blood and contacting blood with ozone, the invention is applicable to the ozonation of other biological fluids such as blood plasma, blood cell suspensions, and suspensions of other cell types.

The invention is disclosed in the appended independent patent claims. Some particular embodiments of the invention are defined in the appended dependent claims.

According to one aspect of the disclosure, an ozonation apparatus for contacting blood with ozone is provided. The apparatus comprises an ozone injector adapted to inject microbubbles of ozone containing gas into a flow of blood in an ozonation zone of an ozone contacting chamber, or ozonation chamber. The apparatus may optionally comprise means for cooling blood entering the ozonation chamber and/or means for warming blood exiting the ozonation chamber.

According to a further aspect of the disclosure, an apparatus for contacting blood with ozone gas is provided. The apparatus has an ozonation chamber, a blood flow inlet, and a blood flow outlet. The ozonation chamber includes an ozone injector 3 configured for connection to a source of ozone containing gas and to inject bubbles of ozone containing gas into a flow of blood through the ozonation chamber. The flow of blood is directed vertically upwards through the blood ozonation chamber during injection. Suitable conduits are provided for directing the flow in relation to gravity so that the flow is vertically upwards at injection of ozone into the blood. The ozonation chamber and the ozone injector are configured such that the vertically upwards flow of blood through the blood ozonation chamber entrains bubbles of ozone containing gas into said flow of blood for said ozonation. The gas bubbles become dissolved in the blood when entrained therein.

According to another aspect of the disclosure, a blood ozonation system is provided. The system comprises the ozonation apparatus, a source of ozone connected to the ozone injector, conduits for receiving blood into and delivering blood from the apparatus, and pumping means for pumping blood through the system. The system optionally comprises cooling means for cooling the blood before entering the ozonation apparatus and/or warming means for warming ozonated blood leaving the ozonation apparatus.

According to yet another aspect of the disclosure, a method for contacting blood with ozone is provided. The method involves contacting blood with micro-sized bubbles of a gas containing ozone. The blood is at a temperature of less than 12° C. when contacted with the microbubbles, the microbubbles have a mean diameter of less than 5 µm.

According to yet another aspect of the disclosure, a method for contacting blood with ozone is provided. The method involves receiving blood, cooling the blood to a temperature of less than 12° C., contacting the chilled blood with microbubbles of a gas containing ozone, optionally warming the blood to a warmed temperature, and delivering the blood to a storage container or storage vessel.

According to yet another aspect of the disclosure, a method for treating a patient suffering from microbial infection is provided. The method involves receiving blood from the patient, cooling the blood to a temperature of less than 12° C., contacting the chilled blood with microbubbles of a gas containing ozone, warming the blood, and returning the blood to the patient. The method is advantageously performed using the system or apparatus of the disclosure.

Features for the second and subsequent aspects of the disclosure are as for the first aspect mutatis mutandis.

Unless otherwise defined, all terms used herein, including technical and scientific terms, have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The term "microorganism" as used herein is synonymous with "microbe" and means any microorganism including bacteria, virus, fungi or yeast, and including spores or dormant forms of such a microorganisms.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1:
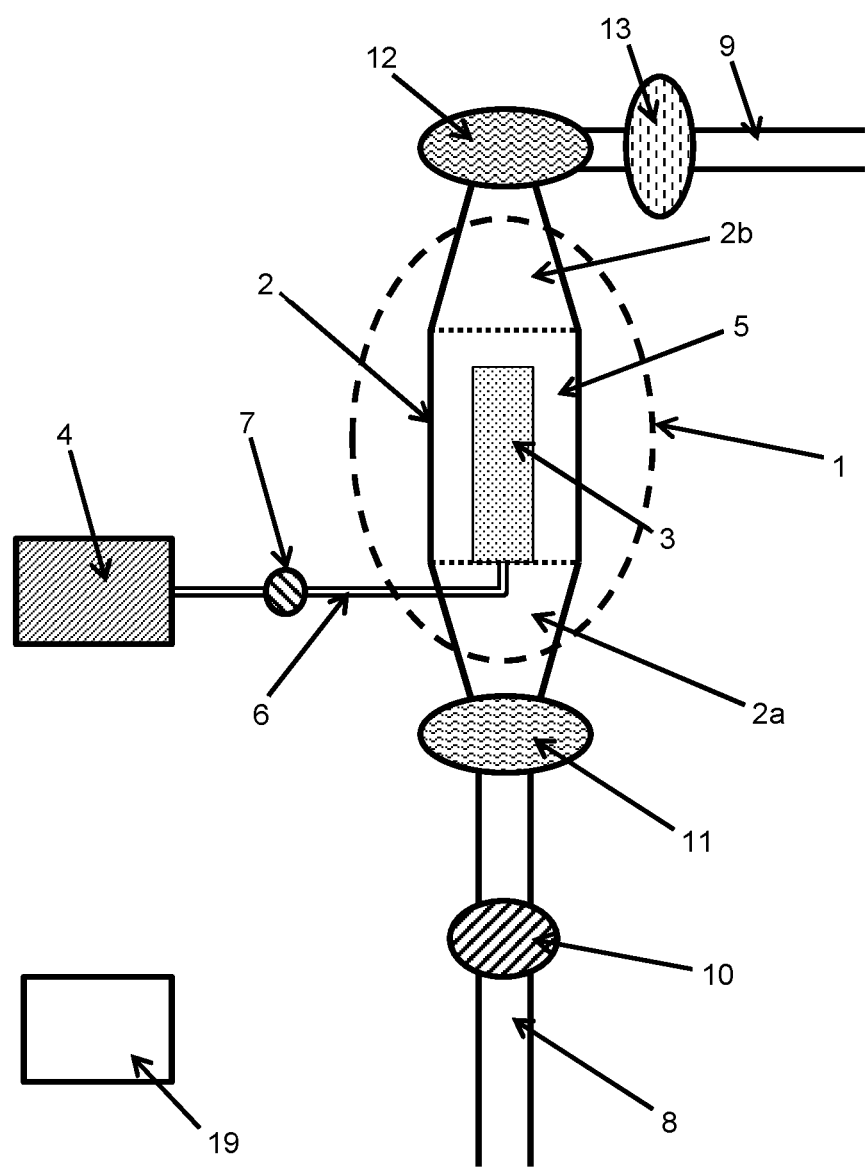
FIG. 1 is a schematic of a first embodiment of an ozonation system comprising an apparatus for contacting blood with ozone.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

A first embodiment of an ozonation system according to the invention is shown in FIG. 1. The apparatus comprises an ozonation apparatus 1 comprising an ozonation chamber 2 comprising an inlet 2a and an outlet 2b, and an ozone injector 3. The ozone injector 3 is configured to be connected to a source of ozone gas 4.

The source of ozone gas may be an ozone generator that produces ozone from oxygen that may produce a gas mixture that contains ozone and oxygen at a certain ratio. Alternative gaseous ozone sources may be provided as known to the skilled person.

The ratio of ozone to oxygen in the gas mixture may for example range from 5% to 20% ozone and from 95% to 80% oxygen. Preferable values of an ozone to oxygen ratios are 5/95, 10/90, 15/85 and 20/80.

The ozone injector may be made from porous material, for example, from sintered stainless steel. Alternatively or in addition, it may be made from sintered ceramic. Alternatively, or in addition other gas injectors may be provided to provide ozone gas to enrich a flow of blood to be ozonized. Other gas injectors may be nozzle based. The porous material has in examples a uniform mean pore size of less than 5 µm in diameter, such as 4 µm, 3 µm, 2 µm, 1 µm, 0.5 µm, or 0.2 µm. The pore size is preferably between about 0.2 µm and about 2.0 µm.

The ozone gas injector 3 may further comprises a flow meter, pressure valve, pressure sensor, and/or controlling element to facilitate monitoring and/or control the pressure and/or flow rate of gas being injected.

The embodiment shown in FIG. 1 shows an ozonation apparatus 1 comprising a porous ozone injector 3 inside an ozonation chamber 2. The ozone injector is cylindrical in the example. The ozonation chamber is configured to guide a flow of blood around the porous microbubble releasing surface of the ozone injector 3. In the example, the ozone injector is cylindrical. Preferably, the cylindrical ozone injector 3 is arranged co-axially in the cylindrical ozonation chamber for advantageous ozonation efficiency. A gap exists between the inner wall of the ozonation chamber 2 and the porous bubble releasing surface of the ozone injector 3. The bubble as preferably microbubbles as elucidated herein.

The flow of blood over the microbubble releasing surface is preferably a laminar flow to minimize turbulence in the blood flow.

The blood flow is preferably directed vertically upwards so that gas bubbles entrain in the flow of blood. By directing the flow of gas in a vertical direction, gas bubbles are entrained upwardly. The gas bubbles are also provided to the entire flow of blood, independent of gravity. The gas bubbles are for instance evenly provided around a cylindrical ozone injector. In this manner, portions of blood that are not enriched with gas comprising ozone are avoided. The vertical direction provides thus advantageous (short) time of gas comprising ozone with the flow of blood until the gas is dissolved in the blood. This is important as for instance remaining gas bubbles returned to a patient have to avoided. In addition, foaming of the blood flow is advantageously reduced or avoided by the vertical arrangement of the blood flow.

Compare e.g. horizontal arrangements as described in WO2008/066470, where portions liquid flow below an injector are not well or not at all ozonized as the bubbles raise upwardly along the injector, i.e. the flow portion above the injector is better ozonized than that below.

Figure 2:
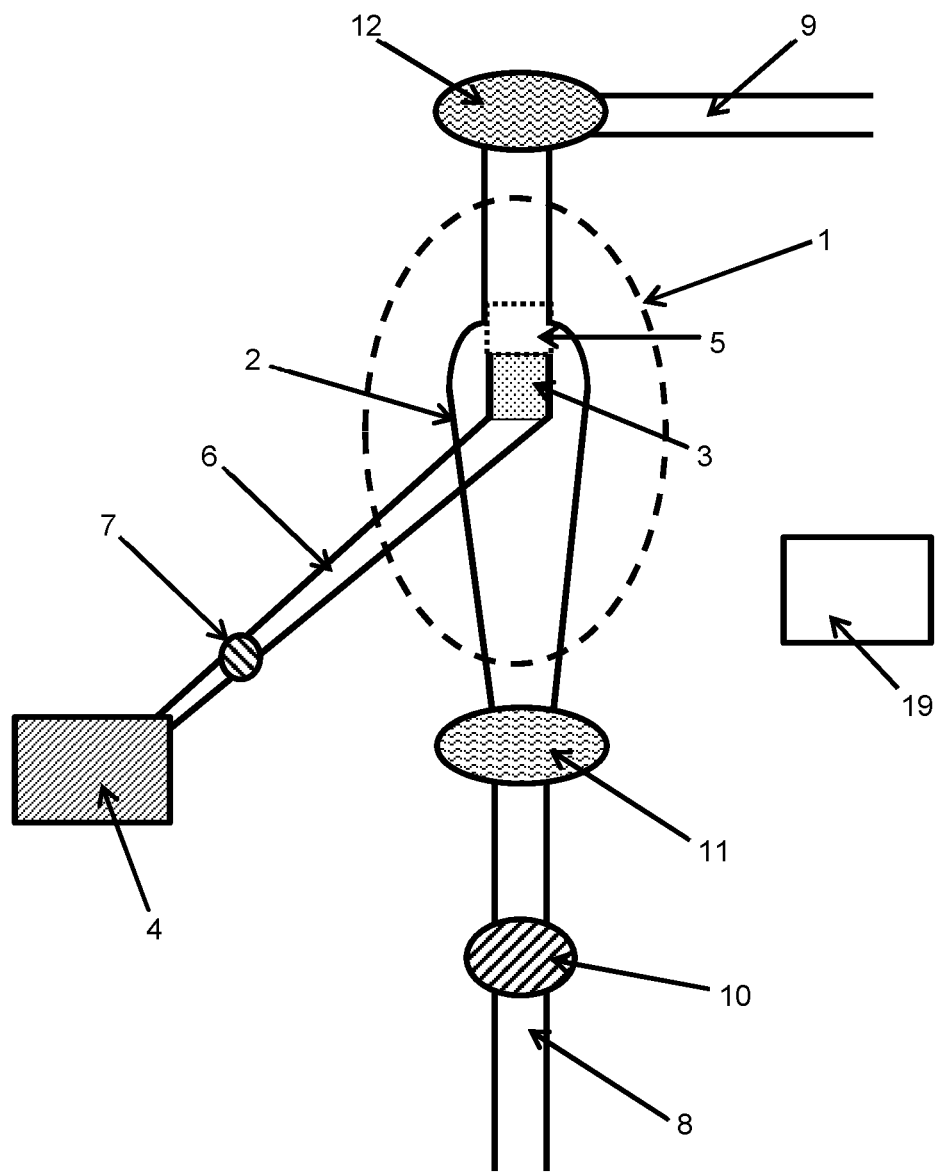
FIG. 2 is a schematic of a second embodiment of an ozonation system comprising an apparatus for contacting blood with ozone.

The shape of the ozone injector 3 need not be cylindrical and not all surfaces of the ozone injector need to be in contact with blood. One alternative configuration is shown in FIG. 2.

The ozone injector 3 is arranged in the ozonation chamber 2 such that blood flow is restricted to pass through ozonation chamber 2 within a maximum distance (d) of a porous surface of the ozone injector 3 from which microbubbles are released. The maximum distance (d) is preferably less than about 2 mm, such as 1.5 mm, 1.0 mm, 0.75 mm, 0.5 mm, 0.25 mm, or 0.1 mm or any distance within this range.

The ozonation chamber 2 and ozone injector 3 are designed to provide an ozonation zone 5 in which micrometer sized bubbles of ozone containing gas mix with and dissolve in a flow of blood.

When blood and ozone containing gas are flowing through the ozonation chamber 1, an ozonation region 5, indicated as the region between the horizontal dashed lines in FIG. 1, exists in which microbubbles are entrained in the blood flow. The bubbles are dissolved in the blood along the entrainment path in the blood flow.

The duration of ozone contacting time, or dwell time, is determined by a number of factors. These factors include the concentration of ozone in the gas, and the flow rate of the gas. Another factor is the temperature of the blood. The temperature at ozonation is preferably controlled in examples of the disclosure. Moreover, the flow rate of the blood is such a factor. Any or all of these factors may be measured, supervised, or controlled to optimize ozonation. The factors maybe computer controlled by controlling gas pressure and flow from the source of ozone 4. Alternatively, or in addition, the operation of blood pumping means 10 may be controlled. Optionally blood cooling means 11 are controlled for advantageous blood ozonation.

A system according to an example of the present disclosure may comprise more than one ozonation apparatus. For example, a plurality of ozone apparatus may be arranged in parallel with respect to the flow of blood.

Alternatively, or in addition, a single ozone apparatus can comprise a plurality of ozone injectors. Each or some of the plurality of ozone injectors may be arranged such that all blood moving through the ozonation chamber passes within the maximum distance (d) of at least one of the ozone injectors.

The ozonation system shown in FIG. 1 additionally may, as illustrated, comprises blood pumping means 10. The blood pumping means 10 are arranged for pumping blood through the apparatus or system from a blood inlet portion 8 to a blood outlet portion 9. Suitable blood pumping means 10 for pumping blood are known in the art and may comprise, for example, a peristaltic pump, a roller pump, or a centrifugal pump. Pumping means 10 may be capable of pumping blood through the system at a suitable flow rate. Suitable flow rates range for example from about 0.1 Liters/hour to about 12 Liters/hour.

The system may also comprise an ozone source 4, such as a medical grade ozone generator. The ozone generator is fluidly connected to the ozone injector 3 by a gas conduit 6. The gas conduit 6 may comprise a one-way valve 7 to prevent backflow of blood into the ozone generator 6. Such backflow may occur in case of, for example, a sudden pressure drop in the gas conduit 6.

The ozone source 4 is preferably capable of delivering ozone at a constant pressure. The ozone source 4 is preferably capable of delivering at least 10% ozone at such a constant pressure. The constant pressure of gas is at least 0.1 bar and preferably up to 0.5 bar, 0.75 bar or 1.0 bar at the ozone injector 3.

The system may additionally comprise a source of one or more inert gasses that may be mixed with the ozone containing gas before reaching the ozone injector. Examples of inert gasses include nitrogen and helium.

The blood contacting portions of the system may preferably be made of any suitable biocompatible materials. Such materials include materials typically used to transfer or store blood, such as those used in tubing for transfusions or blood conducting portions of heart and lung machine or apheresis machines.

The blood entry portion 2 may comprise or be connectable to means for receiving blood from a patient such as a hollow needle for insertion in to a vein.

Alternatively or additionally, blood entry portion 2 may comprise means for receiving blood from a container of blood. Such container may include a bag or bottle or an extracorporeal blood circulation device such as an apheresis machine, dialysis machine, or heart and lunch machine.

The ozonation system may comprise blood cooling means 11 positioned upstream of ozonation apparatus inlet 2a and configured to cool the blood to a chilled temperature of less than 12° C. before the blood enters the ozonation apparatus 1.

The blood cooling means 11 may comprise any suitable blood heat exchanger used in the medical arts to cool blood and may be configured for computer control of the temperature of the blood entering the ozonation chamber 2.

The blood cooling means 11 is preferably controllable to cool said blood to a temperature of between about 4° C. and about 12° C., to produce chilled blood that is contacted with ozone containing gas in the ozonation chamber 2.

It is understood that cooling is a relative term. If for instance blood entering into the ozonation system has a temperature lower than desired, e.g. lower than between about 4° C. and about 12° C., it maybe provided to actually heat the blood to this preferred temperature range. This may be the case for frozen blood preservatives, e.g. frozen blood plasma. Cooling can be understood a term relative to ambient room temperature. Cooling is also relative physiological body temperature if blood is input to the ozonation system at body temperature from a patient.

At ozonation in the ozonation chamber, the blood thus has preferably a temperature of less than 12° C. It preferably has a temperature between about 4° C. and about 12° C. The chilled blood is then contacted at this temperature with ozone containing gas in the ozonation chamber 2.

Additionally or alternatively, the ozonation system may comprise blood warming means 12. The blood warming means is preferably positioned downstream the ozonation chamber. The blood warming means is for example positioned downstream of the outlet 2b from the ozonation apparatus 1. The blood warming means is configured to warm ozonated blood to a temperature above the blood temperature in the ozonation chamber 2.

The blood warming means 12 may be configured to warm blood to a body temperature of a human or nonhuman animal, e.g. between about 24° C. to about 39° C.

Blood warming means 12 may additionally or alternatively be configured to adjust the temperature of the blood to a storage temperature. It is understood that warming is a relative term. If for instance blood leaving the ozonation system has a temperature higher than desired to exit the apparatus or system, it maybe provided to actually, potentially further, cool the blood to this desired temperature. This may be the case when it is desired to provide ozonated frozen blood preservatives, e.g. frozen blood plasma, with advantageous storage properties compared to not ozonated blood products.

Blood warming will in most examples include feeding heat energy to the ozonated blood to increase the temperature thereof.

Blood warming means 12 may be computer controlled similarly to blood cooling means 11.

The system may comprise a blood processing unit 13 comprising means for removing bubbles, preferably downstream the ozone injector. Alternatively, or in addition, the system may comprise a blood processing unit 13 comprising means for removing foam, preferably downstream the ozone injector. Alternatively, or in addition, the system may comprise a blood processing unit 13 comprising means for removing thrombi, preferably downstream the ozone injector. In this manner, undesired bubbles, foam, thrombi, and/or other material may be suitably removed. The treatment may be at least partially be done upstream the ozonation chamber. The treatment is preferably done downstream (relative blood flow) the ozonation chamber, for instance before the blood can be delivered to a patient or to a blood storage container.

Blood processing unit 13 may comprise, for example, a filter for removing particles. Alternatively, or in addition, the blood processing unit 13 may comprise a blood reservoir comprising an inlet region separated from an outlet region by a membrane that is permeable for blood, but impermeable for air bubbles.

A blood processing unit 13 downstream the ozonation chamber may be particularly useful in embodiments of the invention used to ozonate blood that is to be delivered to a patient.

All or parts of the apparatus and/or system may be combined with and/or controlled by a computerized control system 19. The computerized control system 19 may be electrically coupled to sensors, actuators, valves, and/or switches in the ozonation system.

The control system 19 may comprise software having code segments configured to control operational parameters of the apparatus. Operational parameters include parameters such as blood and gas flow rates and pressures, the concentration of ozone and other gasses in the ozone containing gas, blood temperature in the different portions of the apparatus, and blood flow rates in various portions of the apparatus and/or system conduit based upon sensor data received from pressure, flow, temperature, and/or chemical sensors provided in various portions of the apparatus.

FIG. 2 shows an example of an ozonation system comprising an alternatively configured ozonation apparatus 1. Only the top surface of the ozone injector 3 is in contact with blood and injects microbubbles of ozone containing gas into a flow of blood that entrains the injected microbubbles. An ozonation region 5 is located directly above the ozone injector 3 in which the microbubbles completely dissolve in the blood.

Without intending to be bound by theory, it is believed that the ozone is also entirely consumed by chemical reactions with the blood within the ozonation region 5.

The ozonation chamber 2 is configured such that all of the blood flow passes within a maximum distance (d) from the upper surface of the ozone injector 3. The maximum distance (d) is preferably less than about 2 mm, such as 1.5 mm, 1.0 mm, 0.75 mm, 0.5 mm, 0.25 mm, or 0.1 mm or any distance within this range.

Alternatively, the diameter of blood flow can be narrowed above the ozone injector 3 such that a flow of blood entrains a flow of microbubbles in an ozonation zone 5 above the injector.

With such an embodiment, the maximum distance from the surface of the ozone injector 3 may be greater than in other embodiments. The diameter of the flow in the ozonation zone 5 is preferably less than about 2 mm, such as 1.5 mm, 1.0 mm, 0.75 mm, 0.5 mm, 0.25 mm, or 0.1 mm or any distance within this range.

Figure 3:
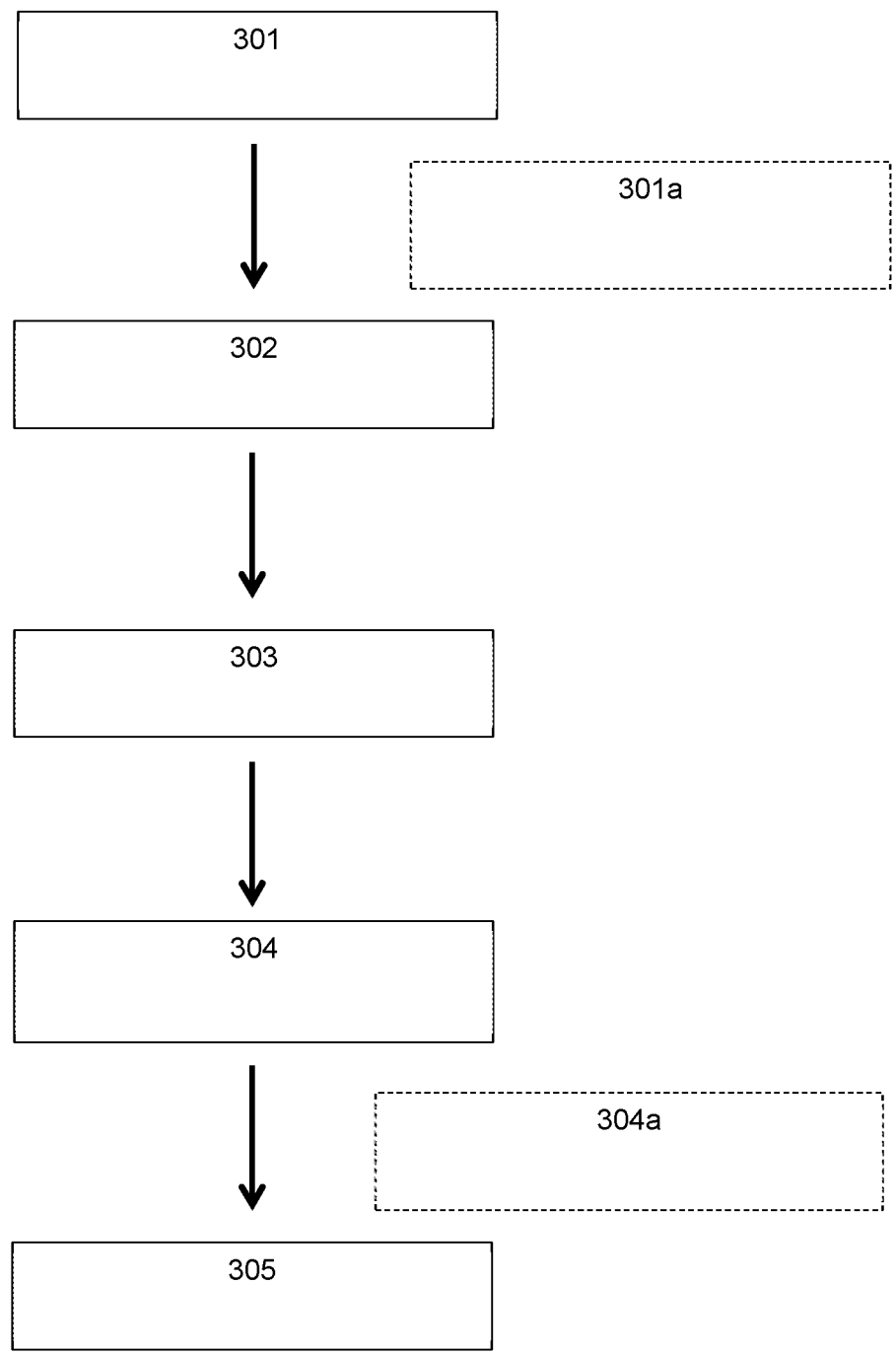
FIG. 3 is a flow chart of method steps for a method for contacting blood with ozone.

In one aspect, the present disclosure relates to a method for contacting blood with ozone (FIG. 3). In a first example, the method comprises receiving a flow of blood 301 into an ozonation system. The method may include injecting microbubbles of ozone containing gas 303 into the flow of blood. Further, the method may include delivering the ozonated blood from the system 305. Preferably, the blood is at a temperature of less than 12° C. during the injecting of ozone. Ozone containing gas is preferably provided as microbubbles that have a mean diameter of less than 5 μm. The temperature of the blood during ozone injection is preferably between about 4° C. and about 10° C., such as 5° C., 6° C., 7° C., 8° C., or 9° C.

The ozone containing gas is normally produced by an ozone generator that produces a mixture of ozone and oxygen comprising between 5% and 20% ozone, a range and ratio as described above.

The concentration of ozone in the ozone containing gas injected into the flow of blood is preferably less than 10 grams/m$^3$ and more preferably less than 5 grams/m$^3$. Preferably, the concentration of ozone in the ozone containing gas is at least 1 gram/m$^3$.

The pressure of gas being injected may be for example, at least 0.1 bar and preferably up to 0.5 bar, 0.75 bar or 1.0.

The ratio of the volumetric flow rate of blood and the volumetric flow rate of ozone containing gas may be adjusted to be in a range of from about 10:1 to about 50:1.

The volumetric flow rate of blood may be in the range of from 0.1 Liters/hour to 12 Liters/hour, for example 3 Liters/hour to 6 Liters/hour.

The delivered dose of ozone in the blood flow is less than 10 ppm, and may be for example, 1 ppm, 2 ppm, 3 ppm, 4 ppm, 5 ppm, 6 ppm, 7 ppm, 8 ppm, or 9 ppm.

The flow of blood is preferably a laminar flow to minimize turbulence.

The flow rates and pressures are controlled or set such that the microbubbles have a substantially uniform mean diameter of less than 5 μm in diameter.

The flow rates and pressures are controlled or set such that the microbubbles completely dissolve in the flow of blood in less than 10 seconds, preferably less than 5 seconds, and more preferably less than 2 seconds.

Controlling the flow and pressure of the ozone containing gas and blood flow rate in this way can prevent the microbubbles from coalescing into larger bubbles so that essentially all of the microbubbles entrained in the blood flow have the desired diameter.

If the method is to be performed on blood from a patient or other source of blood that has a temperature higher than the ozonation temperature, the method may further comprise cooling the blood 302 before ozone is injected into the flow of blood 303.

If the blood is to be returned to a patient or stored at a temperature above the ozonation temperature, the blood may be warmed 304 before being delivered from the system 305.

If the ozonated blood is to be stored, warming the blood may not be necessary, or alternatively cooling is provided as describe above.

The flow of blood received into the ozonation system may optionally be pre-treated 301a, for instance by a blood processing unit upstream the ozonation location. Alternatively or in addition, for example, an anticoagulant or other drug may be added to the blood flow. Alternatively, or in addition, addition of such substance may be provided to ozonated blood, i.e. downstream the ozonation location.

Extracorporeal treatment of blood introduces a possible undesired blood tampering, such as bubble formation, blood foaming, and the formation of clots or precipitates. The method may therefore include one or more post treatment processing steps 304a to remove foam, bubbles, clots, and/or precipitates, as described above.

Blood ozone contacting time and temperature may be optimized for killing particular microorganisms, or microbes.

The contacting may be comprise the administration of drugs that may have an additive or synergistic effect with the ozone to kill microbes and/or a protective effect to reduce unwanted or adverse effects associated with contacting blood with an ozone containing gas.

The present invention has been described above with reference to specific embodiments. However, other embodiments than the above described are equally possible within the scope of the invention as defined in the appended patent claims.

The invention claimed is:

1. An apparatus for contacting blood with ozone gas, said apparatus comprising:
    an ozonation conduit, a blood flow inlet, and a blood flow outlet wherein:
    said ozonation conduit comprises an ozone injector arranged within said conduit and is configured for connection to a source of ozone containing gas and to inject bubbles of ozone containing gas directly into a flow of blood through the ozonation conduit, wherein the flow of blood is vertically upwards through the ozonation conduit during injection, and
    said ozonation conduit and said ozone injector are configured such that the vertically upwards flow of blood through the ozonation conduit entrains said bubbles of ozone containing gas into said flow of blood until the ozone containing gas is dissolved in said blood,
    wherein said ozone injector is configured to inject said bubbles of ozone into said flow of blood to reduce or avoid foaming of the blood by the vertically upwards blood flow, wherein
    said ozone injector is a porous ozone injector; and
    wherein said bubbles are microbubbles having a mean diameter of less than 5 μm.

2. The apparatus of claim 1, wherein said porous ozone injector is cylindrical.

3. The apparatus of claim 2, wherein the cylindrical porous ozone injector is arranged co-axially with the ozonation conduit.

4. The apparatus of claim 2, wherein the ozonation conduit comprises an inner wall, wherein said porous ozone injector comprises a porous bubble releasing surface, and wherein a gap exists between said inner wall and the porous bubble releasing surface of the porous ozone injector.

5. The apparatus of claim 1, wherein the apparatus comprises a cooling unit configured to cool a blood flow entering said ozonation conduit.

6. The apparatus of claim 5 wherein the cooling unit is configured to cool a blood flow entering said ozonation conduit to a temperature of less than 12° C.

7. The apparatus of claim 1, wherein said ozone injector is a microporous ozone injector that has a uniform mean pore size of less than 2 μm.

8. The apparatus of claim 1, wherein said ozone injector comprises a sintered stainless steel or a sintered ceramic through which said ozone containing gas is injectable to provide said bubbles of ozone containing gas.

9. The apparatus of claim 1, wherein said ozonation conduit is shaped to provide a laminar blood flow around said ozone injector.

10. A system for ozonating blood comprising the apparatus of claim 1 and further comprising a pump configured to pump blood through said apparatus and a source of ozone containing gas fluidically coupled to said ozone injector, wherein
    said ozone injector is a porous ozone injector, and wherein said porous ozone injector is cylindrical.

11. The system of claim 10, wherein the system comprises a cooling unit configured to cool a blood flow entering said apparatus.

12. The system of claim 11 wherein the cooling unit is configured to cool a blood flow entering said apparatus to a temperature of less than 12° C.

13. The system of claim 10, wherein the system comprises a warming unit configured to warm a blood flow exiting said apparatus.

* * * * *